US012539381B2

(12) United States Patent
Ishikita

(10) Patent No.: US 12,539,381 B2
(45) Date of Patent: Feb. 3, 2026

(54) SUCTION-TARGET GUIDE PIPE AND SUCTION-TARGET SUCTION SYSTEM

(71) Applicant: Naoyuki Ishikita, Niigata (JP)

(72) Inventor: Naoyuki Ishikita, Niigata (JP)

( * ) Notice: Subject to any disclaimer, the term of this patent is extended or adjusted under 35 U.S.C. 154(b) by 654 days.

(21) Appl. No.: 17/475,845

(22) Filed: Sep. 15, 2021

(65) Prior Publication Data

US 2023/0084589 A1 Mar. 16, 2023

(51) Int. Cl.
*A61M 16/04* (2006.01)

(52) U.S. Cl.
CPC .... *A61M 16/0463* (2013.01); *A61M 16/0402* (2014.02); *A61M 16/0488* (2013.01)

(58) Field of Classification Search
CPC .......... A61M 16/0402; A61M 16/0406; A61M 16/0461; A61M 16/0463; A61M 16/0465–0486; A61M 16/0488; A61M 16/049–0497; A61M 16/0816; A61M 16/0833; A61M 16/0875; A61M 2039/1077–1088; A61M 39/10–1055; A61M 39/12; A61M 39/14; A61M 39/165; A61M 39/20; A61M 2039/1005–1094; A61M 2039/205
USPC ............................ 128/200.24; D24/127–130
See application file for complete search history.

(56) References Cited

U.S. PATENT DOCUMENTS 3,731,684 A 5/1973 Spiegel
4,349,024 A * 9/1982 Ralston, Jr. ........... A61M 39/12 604/905
5,057,093 A 10/1991 Clegg et al.
5,507,535 A 4/1996 Mckamey et al.
5,674,209 A * 10/1997 Yarger .................. A61M 39/20 604/905
5,881,774 A * 3/1999 Utterberg .............. A61M 39/20 215/235
6,609,520 B1 * 8/2003 Carlsen ............. A61M 16/0463 128/207.14

(Continued)

FOREIGN PATENT DOCUMENTS

CN 108175919 A * 6/2018 ............ A61M 16/01
CN 110886872 A 3/2020

(Continued)

OTHER PUBLICATIONS

Translation of CN 108175919-A. Accessed from Espacenet on Jul. 26, 2024. (Year: 2018).*

(Continued)

*Primary Examiner* — Paige Kathleen Bugg
(74) *Attorney, Agent, or Firm* — Future IP LLC; Tomoko Nakajima

(57) ABSTRACT

A suction-target guide pipe that is connected to a suction tube of a suction device includes a guide-pipe main body that includes a connecting portion to be connected to the suction tube, a lid that is provided at an end of the guide-pipe main body and that has an outer peripheral surface and an opening on a distal end side, the outer peripheral surface being formed of a tapered surface whose diameter increases from the distal end to a proximal end, and an end cap that is movable so as to open and close the opening of the lid via a connection cord that is connected to an end of the lid. These features are provided to more easily achieve minimally invasive suctioning of a suction target.

17 Claims, 8 Drawing Sheets

(56) References Cited

U.S. PATENT DOCUMENTS

| | | | | |
|---|---|---|---|---|
| 8,205,764 | B2 * | 6/2012 | Chang | B01L 3/50825 220/259.2 |
| D830,548 | S * | 10/2018 | Kemp | D24/129 |
| 10,758,694 | B2 | 9/2020 | Nye | |
| 11,690,994 | B1 * | 7/2023 | Banik | A61M 39/20 604/103 |
| 2004/0168690 | A1 * | 9/2004 | Payne | B65D 47/0838 128/207.14 |
| 2006/0264814 | A1 * | 11/2006 | Sage | A61M 39/1011 604/890.1 |
| 2008/0121236 | A1 | 5/2008 | Field | |
| 2011/0155135 | A1 | 6/2011 | Chiu | |
| 2013/0018595 | A1 | 1/2013 | Atakhorrami et al. | |
| 2014/0246015 | A1 * | 9/2014 | Einav | A61M 16/0459 128/202.16 |
| 2016/0175201 | A1 * | 6/2016 | Schuessler | F16L 15/04 604/533 |
| 2019/0298164 | A1 * | 10/2019 | Daube | A61B 1/0676 |
| 2020/0061321 | A1 * | 2/2020 | White | A61M 16/0463 |
| 2023/0173246 | A1 * | 6/2023 | Takiguchi | A61M 27/00 604/544 |

FOREIGN PATENT DOCUMENTS

| | | | | |
|---|---|---|---|---|
| CN | 212067304 | U | 12/2020 | |
| CN | 212389798 | U | 1/2021 | |
| DE | 102018210931 | A1 | 1/2020 | |
| EP | 2388042 | A2 | 11/2011 | |
| GB | 2564448 | A * | 1/2019 | A61M 39/10 |
| JP | 3-106371 | A | 5/1991 | |
| JP | 2002219175 | A | 8/2002 | |
| JP | 2008161672 | A | 7/2008 | |
| JP | 2009-297432 | A | 12/2009 | |
| JP | 2012125401 | A | 7/2012 | |
| JP | 2013-126499 | A | 6/2013 | |
| JP | 2013-524202 | A | 6/2013 | |
| JP | 2017-537739 | A | 12/2017 | |
| JP | 2018510714 | A | 4/2018 | |
| JP | 2018-520824 | A | 8/2018 | |
| JP | D167640 | S | 12/2020 | |
| WO | WO2016/100617 | A1 | 6/2016 | |
| WO | WO2016154349 | A1 | 9/2016 | |

OTHER PUBLICATIONS

International Search Report for PCT Patent App. No. PCT/JP2021/033546 (Nov. 16, 2021).

Japanese Office Action for Patent Application No. 2020-118483 (dated Mar. 12, 2024) with its English language translation thereof.

Japanese Decision to Grant a Patent for Application No. 2020-18483 (dated Jul. 30, 2024) with English language translation thereof.

European Search Report for European Patent Application No. 22780967.0 (dated Feb. 11, 2025).

Chinese Office Action for the patent application No. 202280014600.6 (dated Oct. 25, 2025) with English language translation thereof.

European Search Report for European Patent Application No. 21956841.7 (dated May 26, 2025).

* cited by examiner

SUCTION-TARGET GUIDE PIPE AND SUCTION-TARGET SUCTION SYSTEM

BACKGROUND OF THE INVENTION

1. Field of the Invention

The present invention relates to a suction-target guide pipe and a suction-target suction system.

2. Description of the Related Art

It may sometimes be difficult to get a substance (a suction target) out of the human body by coughing or to swallow such a substance, examples of the substance including sputum, saliva, and nasal discharge accumulated in the pharynx due to aging or illness. When such a suction target enters the trachea, the suction target causes dyspnea, suffocation, pneumonia, atelectasis, or the like, and thus, the suction target needs to be suctioned and removed by using, for example, a suction catheter connected to a suction tube of a suction device.

When a substance such as sputum that is to be suctioned by a suction catheter, a sufficient suction effect cannot be obtained unless an end of the suction catheter reaches the suction target. In addition, in this case, there is a possibility that the respiratory tract may be damaged by inserting the suction catheter down to the lower respiratory tract. As an example of the related art for efficiently performing suctioning of sputum, Japanese Unexamined Patent Application Publication (Translation of PCT Application) No. 2013-524202 ([0017]) discloses a collecting device that guides sputum in a patient's lungs to the upper respiratory tract by mechanical insufflation-exsufflation (hereinafter referred to as "MI-E") for mechanically generating positive pressure in the lungs and then applying negative pressure to the lungs and then sucks in and collects the sputum by a suction catheter.

However, in sputum suction using mechanical insufflation-exsufflation (MI-E), since sputum is guided to the upper respiratory tract, minimally invasive sputum suction can be performed, and on the other hand, technical skills are required for mechanical operations and settings. Accordingly, it is desirable that a suction target such as sputum be more easily guided to the side on which the upper respiratory tract is present.

SUMMARY OF THE INVENTION

The present invention has been made in view of the above problem, and it is an object of the present invention to enable minimally invasive suctioning of a suction target by guiding the suction target more easily to the side on which the upper respiratory tract is present.

A suction-target guide pipe according to an aspect of the present invention that is connected to a suction tube of a suction device includes a guide-pipe main body that includes a connecting portion to be connected to the suction tube and a lid that is provided at an end of the guide-pipe main body and that has an outer peripheral surface and an opening on a distal end side, the outer peripheral surface being formed of a tapered surface whose diameter increases from the distal end to a proximal end.

According to the aspect of the present invention, a suction target is guided to the upper respiratory tract side by only bringing the suction-target guide pipe into close contact with a human-body-wearable ventilation member such that the suction-target guide pipe and the human-body-wearable ventilation member communicate with each other after the suction-target guide pipe has been attached to an end of the suction tube of the suction device, so that minimally invasive suctioning of the suction target can be efficiently performed.

A suction-target suction system according to another aspect of the present invention that sucks in a suction target in a living body includes a suction device that includes a suction tube and the above-described suction-target guide pipe that is connected to an end of the suction tube.

According to the other aspect of the present invention, a suction target is guided to the upper respiratory tract side by bringing the suction-target guide pipe into close contact with a human-body-wearable ventilation member such that the suction-target guide pipe and the human-body-wearable ventilation member communicate with each other after the suction-target guide pipe has been attached to an end of the suction tube of the suction device, so that minimally invasive suctioning of the suction target can be easily performed.

According to the present invention, minimally invasive suctioning of a suction target can be achieved by more easily guiding the suction target to the side on which an upper respiratory tract is present.

DESCRIPTION OF THE PREFERRED EMBODIMENTS

Preferred embodiments of the present invention will be described in detail below. Note that the embodiments, which will be described below, do not unreasonably limit the scope of the present invention described in the claims, and not all of the configurations in the descriptions of the embodiments are essential as solutions of the present invention.

Figure 1:
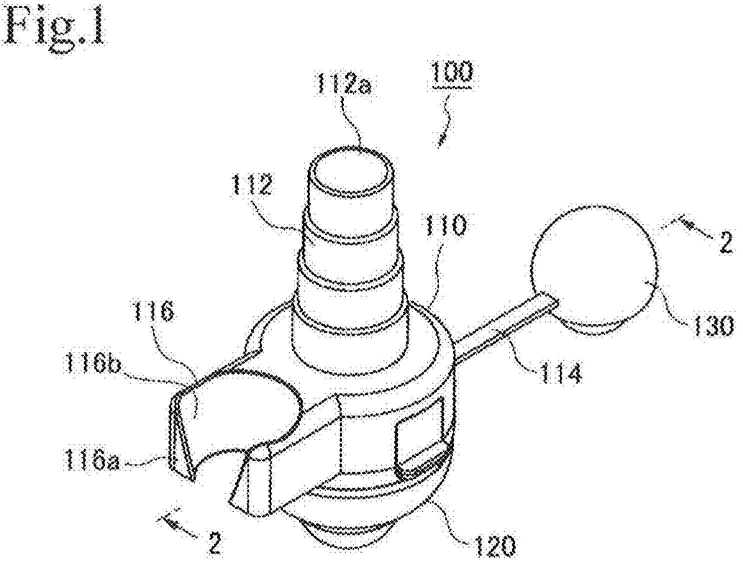
FIG. 1 is a perspective view illustrating a usage state of a suction-target guide pipe according to an embodiment of the present invention.
Figure 2:
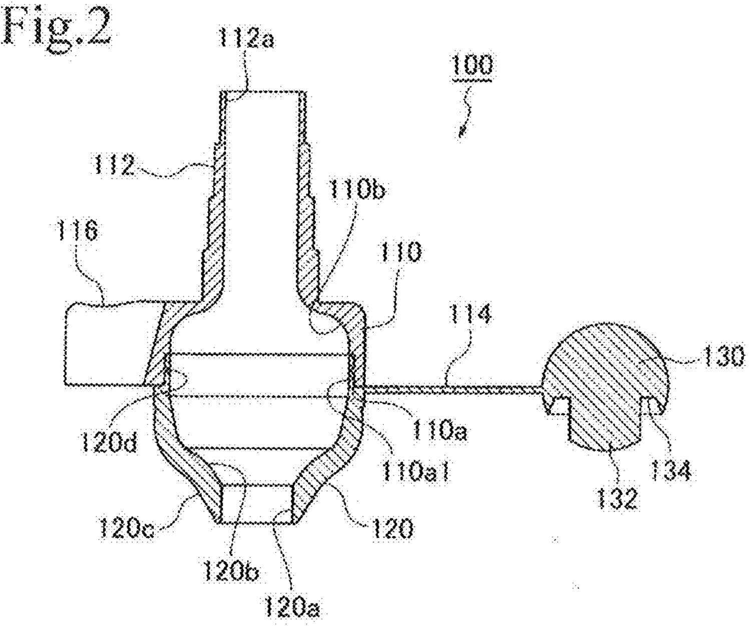
FIG. 2 is a cross-sectional view taken along line 2-2 of FIG. 1.
Figure 3:
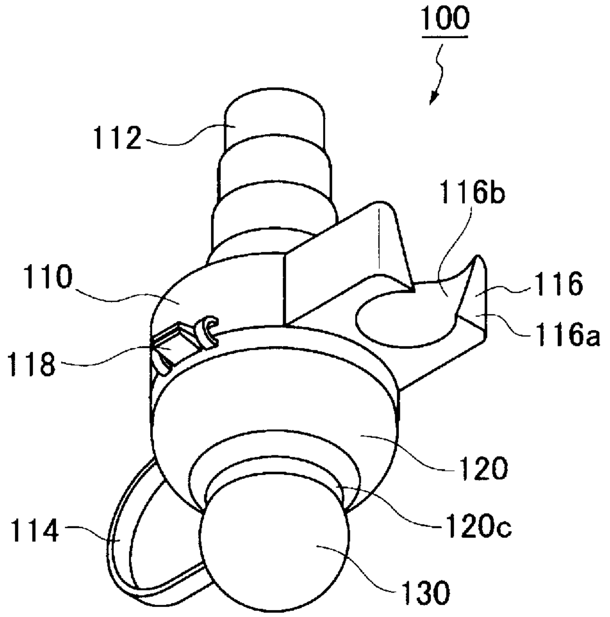
FIG. 3 is a perspective view illustrating an unused state of the suction-target guide pipe according to the first embodiment of the present invention.

First, the schematic configuration of a suction-target guide pipe according to the first embodiment of the present invention will be described with reference to the drawings. FIG. 1 is a perspective view illustrating a usage state of the suction-target guide pipe according to the first embodiment of the present invention. FIG. 2 is a cross-sectional view taken along line 2-2 of FIG. 1. FIG. 3 is a perspective view illustrating an unused state of the suction-target guide pipe according to the first embodiment of the present invention.

When a substance to be suctioned (hereinafter referred to as "suction target") that is, for example, a body fluid such as sputum is suctioned and removed from a patient's respiratory tract including the lower respiratory tract, a suction-target guide pipe 100 of the present embodiment is used as a member that is attached to an end of a suction tube connected to a suction device (a stationary or portable sputum aspirator) so as to guide the suction target to the side on which the upper respiratory tract is present by using the suction force (negative pressure) of the suction device. As illustrated in FIG. 1, the suction-target guide pipe 100 includes a guide-pipe main body 110, a lid 120, and an end cap 130.

The guide-pipe main body 110 includes a connection pipe 112 formed on a surface thereof, and the connection pipe 112 serves as a connecting portion that is connected to the suction tube. In addition, as illustrated in FIG. 2, a portion of the guide-pipe main body 110 that faces the connection pipe 112 on the opposite side has an opening 110*a* whose inner diameter is, for example, about 17 mm, and an inner peripheral surface 110*b* of the guide-pipe main body 110 is a continuous curved surface extending toward the proximal end of the connection pipe 112. As illustrated in FIG. 2, the guide-pipe main body 110 has an engagement recess 110*al* formed on the proximal end side, and an engagement projection 120*d* of the lid 120 that is formed on the proximal end side can be fitted into the engagement recess 110*a*1. As illustrated in FIG. 2, the inner peripheral surface 110*b* of the guide-pipe main body 110 is a gently curved surface whose diameter decreases from the upper end side of the engagement recess 110*al* to the proximal end side of the connection pipe 112.

The connection pipe 112 of the guide-pipe main body 110 has a shape whose diameter decreases toward the distal end of the connection pipe 112, and the distal end has an opening 112*a*. The inner diameter of the opening 112*a* is, for example, about 7.0 mm. Note that the shape of the connection pipe 112 is not limited to a shape whose diameter decreases in a stepwise manner toward the distal end as illustrated in FIG. 1 as long as the diameter of the connection pipe 112 decreases toward the distal end.

In addition, in the present embodiment, although the connection pipe 112 is included in the guide-pipe main body 110 so as to serve as a "connecting portion" that is connected to the suction tube, the connecting portion is not limited to the connection pipe 112 that is inserted into the suction tube. In other words, as the "connecting portion" included in the guide-pipe main body 110, for example, a hole into which the suction tube can be inserted so as to be fixed in place may be formed in a surface of the guide-pipe main body 110.

As illustrated in FIG. 1, a holder 116 that is capable of holding a tubular member is provided at an end of the outer periphery of the guide-pipe main body 110 on the lower end side of the guide-pipe main body 110. The holder 116 includes a pair of holding portions 116*a* that project from the end of the lower-end-side outer periphery of the guide-pipe main body 110, and for example, as a tubular member, the suction tube of the suction device can be fixed in place by the holder 116 such that an end of the suction tube faces upward. As illustrated in FIG. 1 and FIG. 2, the holder 116 has an inner peripheral surface 116*b* whose diameter increases from the proximal end side to the distal end side, and the inner peripheral surface 116*b* is an inner tapered surface.

As illustrated in FIG. 3, the lid 120 that allows a suction target, which is to be suctioned, to be introduced into the suction-target guide pipe 100 is connected to the portion of the guide-pipe main body 110, which faces the connection pipe 112, by a hinge mechanism 118 so as to be openable and closable. In other words, the lid 120 is a hinge cap that is movable by the hinge mechanism 118 so as to open and close the opening 110*a* of the guide-pipe main body 110. Note that the lid 120 is not limited to being a hinge cap that is connected to the guide-pipe main body 110 by the hinge mechanism 118, and a different mounting form of the lid 120 may be employed. For example, the lid 120 may be openable and closable with respect to the guide-pipe main body 110 by forming a recess and a projection that engage each other in and on a connection portion of the lid 120 and a connection portion of the guide-pipe main body 110, respectively. Alternatively, the hinge mechanism 118 connecting the guide-pipe main body 110 and the lid 120 to each other does not need to be provided, and the guide-pipe main body 110 and the lid 120 may be separate members.

As illustrated in FIG. 2, the lid 120 has an inner peripheral surface 120*b* that is formed of a curved surface whose diameter decreases from the proximal end side to the distal end side. When the lid 120 is closed with respect to the guide-pipe main body 110, the inner peripheral surface 120*b* becomes a curved surface that is contiguous to the inner peripheral surface 110*b* of the guide-pipe main body 110, and the inner peripheral surface 120*b* of the lid 120 and the inner peripheral surface 110*b* of the guide-pipe main body 110 define a space having a so-called olive shape.

In addition, the lid 120 has an opening 120*a* formed at the distal end thereof, and the inner diameter of the opening 120*a* is, for example, about 4.0 mm. As illustrated in FIG. 2, a tapered surface 120*c* extends from the outer edge of the opening 120*a*, which is formed at the distal end of the lid 120, so as to have a predetermined length while its diameter increases toward the proximal end of the lid 120. The end cap 130 is connected to the lid 120 by a connection cord 114 that is connected to an end of the lid 120, and the end cap 130 is movable so as to open and close the opening 120*a* of the lid 120.

In order to ensure the sealing performance of the end cap 130 with respect to the opening 120*a* of the lid 120, as illustrated in FIG. 2, the end cap 130 has a projection 132 formed at the center thereof so as to close the opening 120*a* of the lid 120 and a groove 134 formed along the outer edge of the projection 132. Note that the configuration of the end cap 130 is not limited to that illustrated in FIG. 2 and may have a different structure.

In order to ensure the sealing performance of the lid 120 with respect to the opening 110*a* of the guide-pipe main body 110, as mentioned above and as illustrated in FIG. 2, the engagement projection 120*d*, which can be fitted into the engagement recess 110*al* formed in the inner edge of the opening 110*a* of the guide-pipe main body 110, is formed at the proximal end of the lid 120 that is located on the side opposite to the side on which the opening 120*a* is formed. Note that the structure on the proximal end side of the lid 120 is not limited to that illustrated in FIG. 2 and may be a different structure.

In the case where the suction-target guide pipe 100 of the present embodiment is used by being connected to the suction tube of the suction device to perform suctioning of sputum or the like, when sputum or the like in the respiratory tract is suctioned as a suction target, the lid 120 is opened with respect to the opening 110*a* of the guide-pipe main body 110. Then, the inner peripheral surface 110*b* of the guide-pipe main body 110 is brought close to and brought into close contact with an end of a tracheal tube, a tracheal cannula, or the like that is attached to a patient so as to perform, by using the suction force (negative pressure) of the suction device, vacuuming (guiding) for moving a suction target such as sputum in the lower respiratory tract, which extends from the trachea to the terminal bronchioles in the lungs, to the upper respiratory tract side. After the suction target has been moved to the upper respiratory tract side, the suction target, such as sputum, guided to the upper respiratory tract side can be suctioned by a suction device such as a suction catheter.

When nasal discharge in the nasal cavity is suctioned as a suction target, as illustrated in FIG. 1 and FIG. 2, the lid 120 covers the opening 110*a* of the guide-pipe main body 110, and the end cap 130 is moved so as to open the opening 120*a*. Then, the tapered surface 120*c* formed at the outer edge of the opening 120*a* of the lid 120 is brought close to and brought into close contact with the nasal cavity. Subsequently, vacuuming for moving the suction target, such as nasal discharge in the nasal cavity, to the front side of the nasal cavity is performed, and in this state, the suction target can be suctioned and removed. Alternatively, the suction target that has been moved to the front side of the nasal cavity by the vacuuming can be suctioned and removed by a suction device such as a suction catheter.

In contrast, when the suction-target guide pipe 100 is not in use, in order to prevent a suction target that remains in a suction tube from flowing backward and falling and prevent foreign matters such as dust from entering the suction-target guide pipe 100, as illustrated in FIG. 3, the lid 120 covers the opening 110*a* of the guide-pipe main body 110, and the end cap 130 serves as a lid and covers the opening 120*a*.

Figure 4:
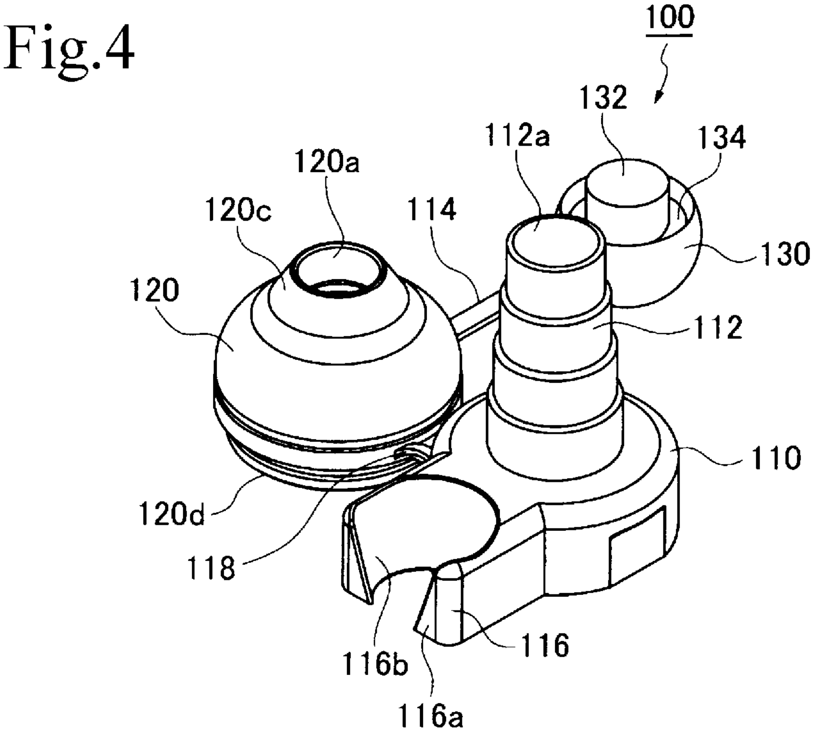
FIG. 4 is a perspective view illustrating an unfolded state of the suction-target guide pipe according to the first embodiment of the present invention.
Figure 5:
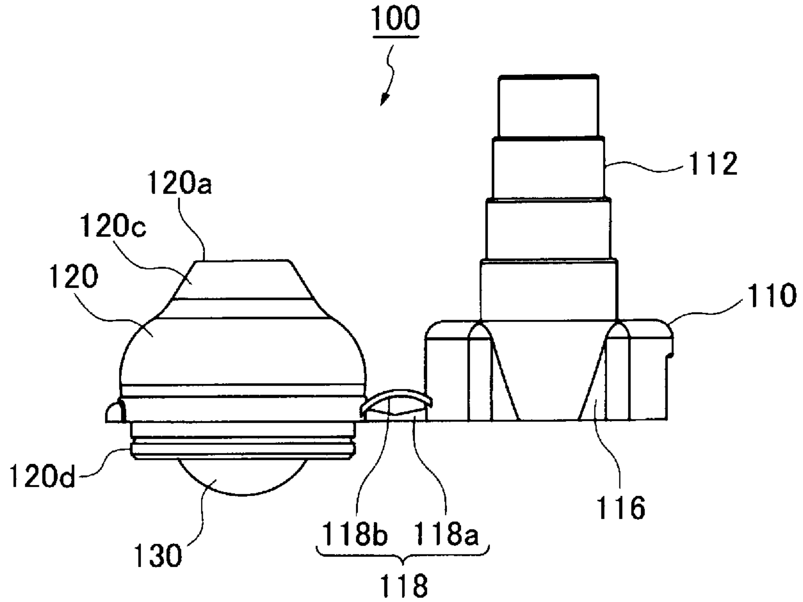
FIG. 5 is a front view illustrating the unfolded state of the suction-target guide pipe according to the first embodiment of the present invention.
Figure 6:
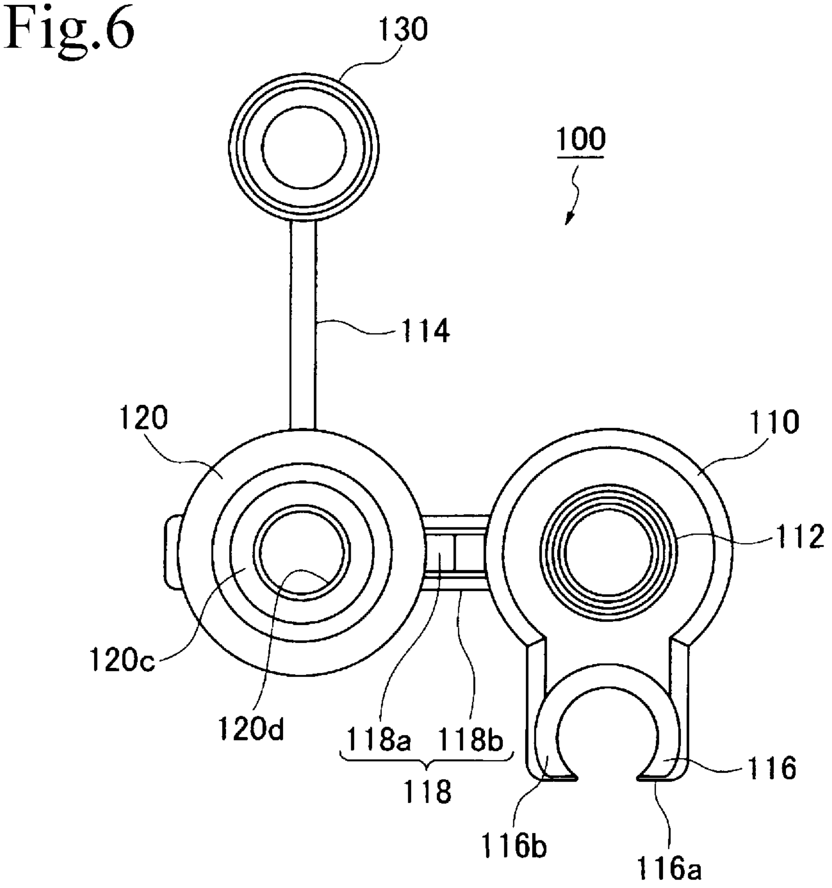
FIG. 6 is a plan view illustrating the unfolded state of the suction-target guide pipe according to the first embodiment of the present invention.
Figure 7:
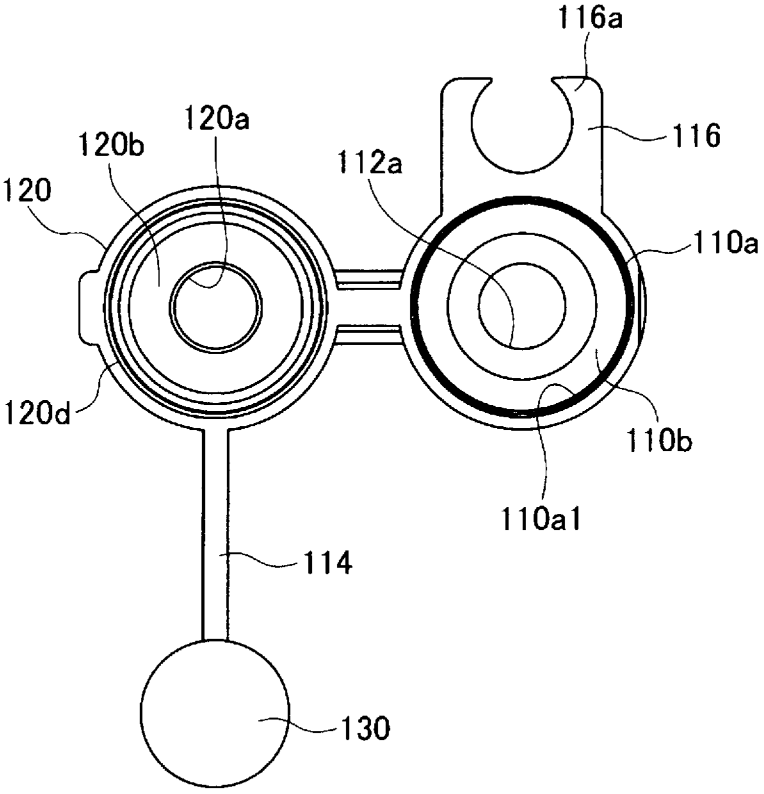
FIG. 7 is a bottom view illustrating the unfolded state of the suction-target guide pipe according to the first embodiment of the present invention.

An unfolded state of the suction-target guide pipe according to the first embodiment of the present invention will now be described with reference to the drawings. FIG. 4 is a perspective view illustrating an unfolded state of the suction-target guide pipe according to the first embodiment of the present invention. FIG. 5 is a front view illustrating the unfolded state of the suction-target guide pipe according to the first embodiment of the present invention. FIG. 6 is a plan view illustrating the unfolded state of the suction-target guide pipe according to the first embodiment of the present invention. FIG. 7 is a bottom view illustrating the unfolded state of the suction-target guide pipe according to the first embodiment of the present invention.

As illustrated in FIG. 4 to FIG. 7, in the suction-target guide pipe 100 of the present embodiment, the guide-pipe main body 110, the lid 120, the hinge mechanism 118, the end cap 130, and the connection cord 114 are formed of an integrally molded body. In other words, the components of the suction-target guide pipe 100 are integrally formed into one molded body by injection molding using a thermoplastic resin such as a polyethylene (PE), polypropylene (PP), polyvinyl chloride (PVC), ABS resin, or acrylic resin (PMMA).

As illustrated in FIG. 6 and FIG. 7, the hinge mechanism 118 is provided so as to be capable of performing opening and closing operations in directions that are perpendicular to a direction in which the holder 116 of the guide-pipe main body 110 is oriented. The hinge mechanism 118 includes a hinge connecting portion 118*a* that connects the guide-pipe main body 110 and the lid 120 to each other and plate springs 118*b* that are arranged on opposite sides of the hinge connecting portion 118*a*. Thus, as illustrated in FIG. 5, when the lid 120 is opened with respect to the guide-pipe main body 110, the lid 120 can be maintained in the open state by the restoring force of the plate springs 118*b*.

As illustrated in FIG. 6 and FIG. 7, the connection cord 114 is provided so as to extend in a direction perpendicular to a direction in which the hinge mechanism 118 of the lid 120 is oriented. More specifically, the connection cord 114 is provided so as to be located at a position facing the holder 116 and so as to extend in the direction perpendicular to the direction in which the hinge mechanism 118 of the lid 120 is oriented when the suction-target guide pipe 100 is viewed in plan view from the connection pipe 112 in a state where the lid 120 is closed with respect to the guide-pipe main body 110.

The components of the suction-target guide pipe 100 of the present embodiment are arranged in this manner, so that the opening and closing operations of the lid 120 with respect to the opening 110*a* of the guide-pipe main body 110 and the opening and closing operations of the end cap 130 with respect to the opening 120*a* of the lid 120 do not interfere with each other. This improves the efficiency with which the opening and closing operations of the lid 120 and the end cap 130 are performed when the suction-target guide pipe 100 is used.

Figure 8:
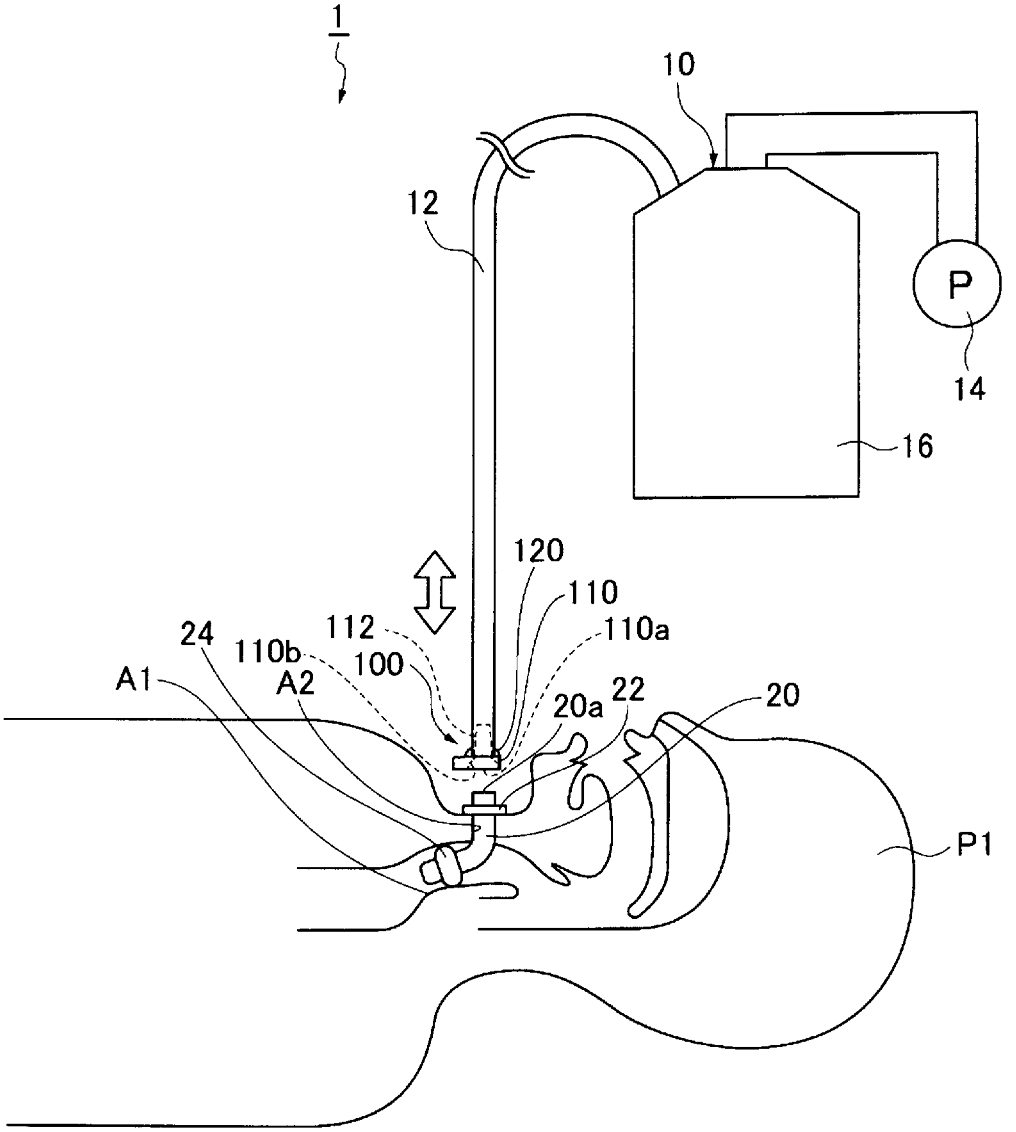
FIG. 8 is a schematic diagram illustrating a configuration of a suction-target suction system according to a first embodiment of the present invention that uses the suction-target guide pipe according to the first embodiment of the present invention.

A suction-target suction system according to the first embodiment of the present invention that uses the suction-target guide pipe 100 and a method of guiding a suction target (hereinafter referred to as "suction-target guiding method") will now be described with reference to the drawings. FIG. 8 is a schematic diagram illustrating the configuration of the suction-target suction system according to the first embodiment of the present invention that uses the suction-target guide pipe 100 according to the first embodiment. Note that FIG. 8 illustrates, as an embodiment of the suction-target guide pipe 100, a suction-target suction system 1, and the suction-target guiding method using the suction-target suction system 1, a state in which sputum, which is a suction target, is suctioned by being guided through a tracheal cannula (a ventilation member to be worn on the human body, which will be referred to as a human-body-wearable ventilation member) that is attached to a patient by performing a tracheotomy.

The suction-target suction system 1 is used when suctioning a suction target that is a body fluid or the like such as sputum clogging, for example, a trachea A1, which is an airway of a patient P1 who is a living body, or the lungs (not illustrated). As illustrated in FIG. 8, the suction-target suction system 1 is configured such that the above-described suction-target guide pipe 100 is connected to an end of a suction tube 12 of a suction device 10. The suction device 10 includes a suction pump 14 serving as a negative pressure source that generates a suction pressure in the suction tube 12 made of, for example, a resin having flexibility such as polyurethane and a container 16 that contains a suction target suctioned through the suction tube 12, and the suction device 10 has a function of suctioning a suction target. Note that, in the case of using a portable suction device as the suction device 10, the portable suction device can be used by directly connecting the suction-target guide pipe 100 of the present embodiment thereto, and thus, in this case, the suction tube 12 does not need to be provided. In addition, in the suction-target suction system 1 of the present embodiment, although the suction-target guide pipe 100 is attached to the end of the suction tube 12, a configuration in which the suction-target guide pipe 100 and the suction tube 12 are integrally formed may be employed.

In the present embodiment, for example, the lid 120 of the suction-target guide pipe 100 is opened with respect to the guide-pipe main body 110, and then, as illustrated in FIG. 8, the guide-pipe main body 110 is brought close to a tracheal cannula 20 that is inserted in an incision hole A2 formed in the throat of the patient P1 and fixed in place by a fixing plate 22 and a cuff 24. Then, the inner peripheral surface 110*b* of the guide-pipe main body 110 of the suction-target guide pipe 100 is brought into contact with an end 20*a* of the tracheal cannula 20, and a suctioning operation using the suction device 10 is started. The suction force (negative pressure) of the suction device 10 is transmitted to the tracheal cannula 20 through the suction-target guide pipe 100, so that vacuuming (guiding) for moving a suction target such as sputum in the lower respiratory tract, which extends from the trachea A1 to the terminal bronchioles in the lungs, to the upper respiratory tract side is performed.

In other words, the suction-target suction system 1 and the suction-target guiding method of the present embodiment move a suction target such as sputum suctioned through the tracheal cannula 20 to the upper respiratory tract side by bringing the suction-target guide pipe 100 connected to the suction tube 12 into close contact with the end 20*a* of the tracheal cannula 20, which is inserted in the incision hole A2 so as to reach the trachea A1. After that, the suction target such as sputum that has been guided in the trachea A1 to the upper respiratory tract side is suctioned by a suction catheter.

Note that, in the present embodiment, the diameter of the opening 110*a* of the suction-target guide pipe 100 is slightly larger than the diameter of the end 20*a* of the tracheal cannula 20 so as to allow leeway. More specifically, in the case where the outer diameter of the end 20*a* of the tracheal cannula 20 is, for example, 15 mm, the inner diameter of the opening 110*a* of the suction-target guide pipe 100 is set to 17 mm, so that the tracheal cannula 20 and the suction-target guide pipe 100 may be easily brought into close contact with each other, and the probability that a patient will have a suffocation accident as a result of an excessive operation for bringing these members into close contact with each other, that is, connection of these members, can be reduced.

In this manner, in the suction-target suction system 1 and the suction-target guiding method of the present embodiment, the suction-target guide pipe 100 performs vacuuming for moving a suction target such as sputum in the lower respiratory tract, which extends from the trachea A1 to the terminal bronchioles, to the upper respiratory tract side, and then the suction target that has been guided in the trachea A1 to the upper respiratory tract side is suctioned by a suction device such as a suction catheter. In other words, the suction-target guide pipe 100 of the suction-target suction system 1 of the present embodiment is used as an attachment that guides a suction target such as sputum in the lower respiratory tract, which extends from the trachea A1 to the terminal bronchioles, toward a portion of the trachea A1 that is located on the upper respiratory tract side in order to make it easier to suction the suction target by a suction device such as a suction catheter.

As an application example of the suction-target guiding method of the present embodiment, a method of suctioning sputum that can be performed by using the suction-target suction system 1 will now be described. When a suction target such as sputum is suctioned from the lower respiratory tract of the patient P1, a stethoscopic examination of the lungs or the like of the patient P1 is performed by using a stethoscope first, and then, pressure ventilation is performed by using, for example, a bag valve mask at a positive pressure of 40 $cmH_2O$ for five seconds so as to inflate the lungs. In this case, if atelectasis has occurred in a portion that is further toward the peripheral side than the portion in which the suction target is stored, it may sometimes be difficult to squeeze the suction target up toward the upper respiratory tract side even by performing vacuuming because there is no air in the peripheral lung. Accordingly, in the present embodiment, pressure ventilation is performed before the suctioning operation.

When sputum suctioning is required, the breathing state of the patient P1 is not favorable, and the blood oxygen saturation level is often low. In addition, during the sputum suctioning, the patient P1 is unable to breathe and is likely to experience hypoxia. Accordingly, in the present embodiment, when the above-mentioned pressure ventilation is performed before the suction operation, the pressure ventilation is performed by mixing oxygen so as to stabilize the patient's condition, and the suctioning operation is started. Note that, although highly-concentrated oxygen may be mixed in the pressure ventilation in order to stabilize the condition of the patient P1 in a short time, if there is no request to perform the pressure ventilation in a short time, the pressure ventilation may be performed with normal air containing oxygen. A pressure ventilation device such as a bag valve mask may be included as a component in the suction-target suction system 1 of the present embodiment.

After that, vacuuming is performed at a negative pressure of, for example, 60 $cmH_2O$ for five seconds so as to deflate the entire lungs, and the suction target such as sputum is guided to the upper respiratory tract side. Then, the suction target such as sputum guided to the upper respiratory tract side is suctioned by a suction device such as a suction catheter. In this case, since atelectasis occurs when the lungs are squeezed by vacuuming, pressure ventilation is performed again at a positive pressure of 40 $cmH_2O$ for five seconds, so that the air is taken into the lungs, and the states of the lungs return to normal. In this manner, in the suction-target suction system 1 of the present embodiment, pressure ventilation is performed before and after the suctioning operation that is performed by deflating the entire lungs by vacuuming with a negative pressure.

In the suction-target guiding method using the suction-target suction system 1 of the present embodiment, the cycle of pressure ventilation with a negative pressure after a stethoscopic examination of the patient P1, vacuuming with a negative pressure, suctioning of a suction target that has been guided to the upper respiratory tract side, and another pressure ventilation with a negative pressure is repeated until the patient P1's symptom is improved. As described above, in the suction-target suction system 1 of the present embodiment, the suction-target guide pipe 100 is connected to the end of the suction tube 12 of the suction device 10, and a vacuuming operation of guiding a suction target in the lower respiratory tract toward the upper respiratory tract side. Then, a suctioning operation of suctioning the suction target, which has been guided to the upper respiratory tract side, by using a suction device such as a suction catheter is performed, so that minimally invasive suctioning of sputum may easily be achieved. In addition, in the present embodiment, pressure ventilation is performed before and after the suctioning operation, so that minimally invasive sputum suctioning that further reduces the amount of pain experienced by the patient P1 may be achieved.

Note that, in the suction-target suction system 1 of the present embodiment, vacuuming is performed by bringing the inner peripheral surface 110*b* of the guide-pipe main body 110 of the suction-target guide pipe 100 connected to the suction tube 12 into contact with the tracheal cannula 20 attached to the throat of the patient P1, and then, a suction target guided to the upper respiratory tract side is suctioned by a suction catheter or the like. However, the suction-target suction system 1 is also applicable to a different situation. For example, in the case where the tracheal cannula 20 is not inserted in the incision hole A2 formed in the throat of the patient P1, the opening 120*a* of the lid 120 on the distal end side may be brought into close contact with the incision hole A2 after the lid 120 has been closed with respect to the guide-pipe main body 110 of the suction-target guide pipe 100, and vacuuming may be performed so as to guide a suction target such as sputum in the lower respiratory tract, which extends from the trachea A1 to the terminal bronchioles, toward the upper respiratory tract side. Then, the suction target, which has been guided to the upper respiratory tract side, may be suctioned and removed by a suction device such as a suction catheter.

Figure 9:
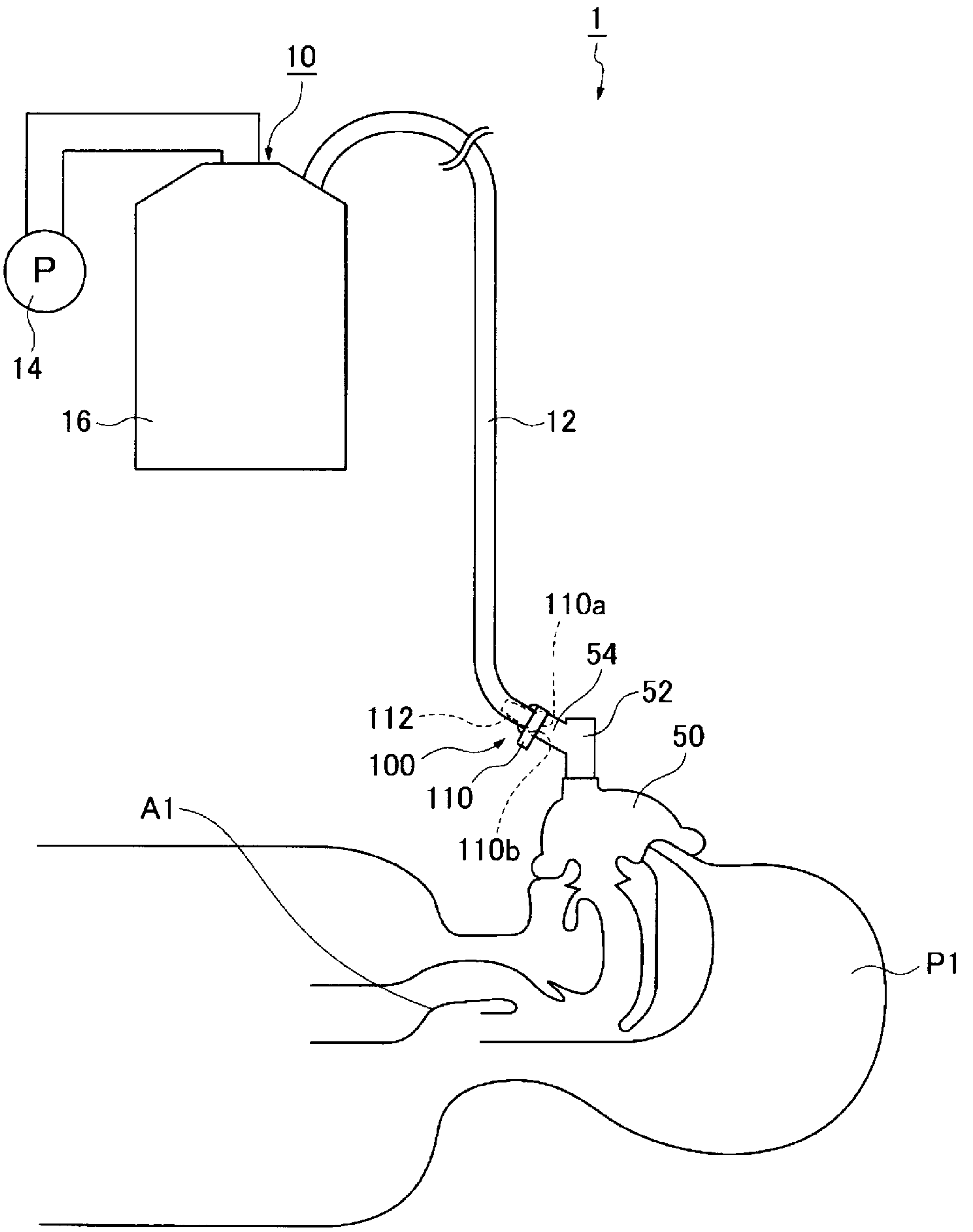
FIG. 9 is a schematic diagram illustrating a configuration of a suction-target suction system according to another embodiment of the present invention that uses the suction-target guide pipe according to the first embodiment of the present invention.

In addition, the suction-target suction system 1 of the present embodiment may be configured as illustrated in FIG. 9 even if a human-body-wearable ventilation member such as the tracheal cannula 20 is not intubated. FIG. 9 illustrates, as an embodiment of the suction-target guide pipe 100, a suction-target suction system 1, and the suction-target guiding method using the suction-target suction system 1, an embodiment in which the suction-target guide pipe 100 connected to the suction tube 12 of the suction device 10 is brought into close contact with a branch port 54 that is branched from a connecting member 52 attached to an end portion of an artificial ventilation mask 50, which covers the oral cavity of the patient P1, so as to guide a suction target. Note that, for example, a mask that covers the patient's nose and mouth can be used as the artificial ventilation mask 50.

Note that, in the present embodiment, the diameter of the opening 110*a* of the suction-target guide pipe 100 is slightly larger than the diameter of the branch port 54 of the connecting member 52 so as to allow leeway. More specifically, in the case where the outer diameter of the branch port 54 of the connecting member 52 is, for example, 15 mm, the inner diameter of the opening 110*a* of the suction-target guide pipe 100 is set to 17 mm, so that the connecting member 52 and the suction-target guide pipe 100 may be easily brought into close contact with each other, and the probability that the patient will have a suffocation accident as a result of an excessive operation for bringing these members into close contact with each other, that is, connection of these members, can be reduced.

As described above, the inner peripheral surface 110*b* of the guide-pipe main body 110 of the suction-target guide pipe 100 is brought into close contact with the branch port 54 of the connecting member 52 of the artificial ventilation mask 50 from the side on which the opening 110*a* of the guide-pipe main body 110 is formed, and a suction target such as sputum in the lower respiratory tract, which extends from the trachea A1 to the terminal bronchioles, is vacuumed, so that the suction target can be guided into the oral cavity of the upper respiratory tract. Thus, the suction target guided into the oral cavity of the upper respiratory tract can be easily suctioned by a suction device such as a suction catheter. In addition, in the present embodiment, by performing vacuuming through the artificial ventilation mask 50, not only a suction target in the oral cavity but also a suction target in the nasal cavity can be guided toward the artificial ventilation mask 50 and can be suctioned.

Figure 10:
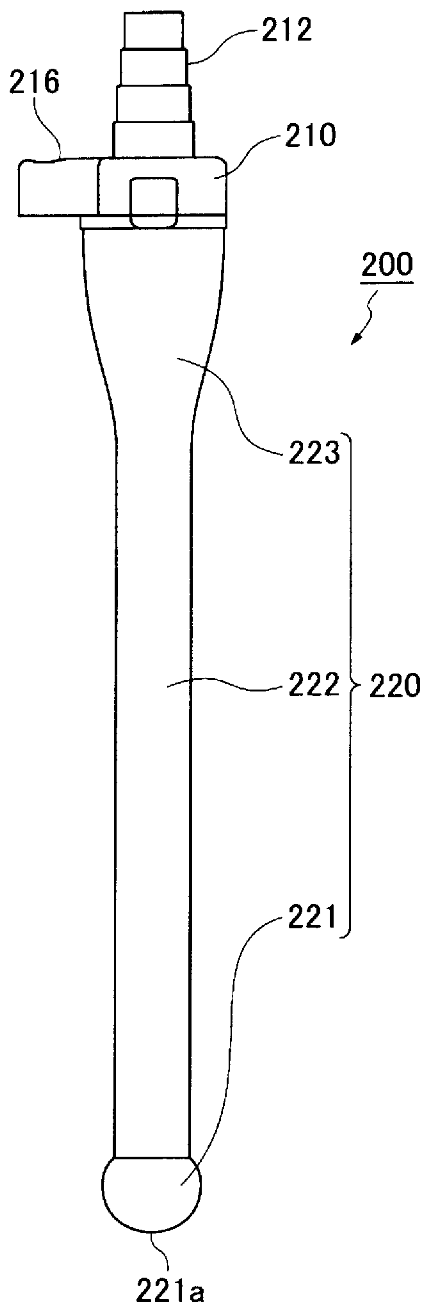
FIG. 10 is a right-hand side view illustrating an unused state of a suction-target guide pipe according to another embodiment of the present invention.

Furthermore, in the present embodiment, if a suction-target guide pipe 200, such as that illustrated in FIG. 10, that is formed as a long cap with a lid 220 having a length of, for example, about 140 mm is used as a suction-target guide pipe that is connected to the suction tube 12, it is not necessary to use a suction device such as a suction catheter. In other words, if the lid 220 that is openable and closable with respect to a guide-pipe main body 210, which includes a connection pipe 212 and a holder 216, includes a distal end portion 221 that has a circular shape and that has an opening 221*a* formed at an end thereof, a proximal end portion 223 that is connected to the guide-pipe main body 210, and a hollow elongated pipe portion 222 that extends between the distal end portion 221 and the proximal end portion 223, a suction target can be guided into the oral cavity and suctioned by using only the suction-target guide pipe 200 that is connected to the suction tube 12.

More specifically, first, the lid 220 is opened with respect to the guide-pipe main body 210 of the suction-target guide pipe 200, and vacuuming is performed by bringing the guide-pipe main body 210 into close contact with the branch port 54 of the connecting member 52 of the artificial ventilation mask 50 so as to guide a suction target such as sputum in the lower respiratory tract of the patient P1 to the upper respiratory tract. After that, the lid 220 having the shape of a long cap is closed with respect to the guide-pipe main body 210, and the artificial ventilation mask 50 is removed from the face of the patient P1. Then, the distal end portion 221 of the lid 220 is directly inserted into the oral cavity of the patient P1. Subsequently, the suction target guided into the oral cavity is suctioned through the opening 221*a* the distal end portion 221 of the lid 220.

As described above, in the suction-target guide pipe 200 of the present embodiment, since the distal end portion 221 of the lid 220 has a circular shape, the probability that the oral cavity will be injured when a suction target is suctioned by inserting the lid 220 into the oral cavity can be reduced. In addition, the suction-target guide pipe 200 of the present embodiment can also be applied, as a so-called olive-shaped pipe, to suctioning of a suction target such as nasal discharge in the nasal cavity. Note that the suction-target guide pipe 200 of the present embodiment is applied as a suction pipe used for suctioning in the oral cavity, and thus, the pipe portion 222 may have, for example, a bent portion that is bent about 75 degrees so as to be easily inserted into the oral cavity. In addition, an end cap that is movable so as to open and close the opening 221*a* of the distal end portion 221 of the lid 220 may be provided.

Figure 11:
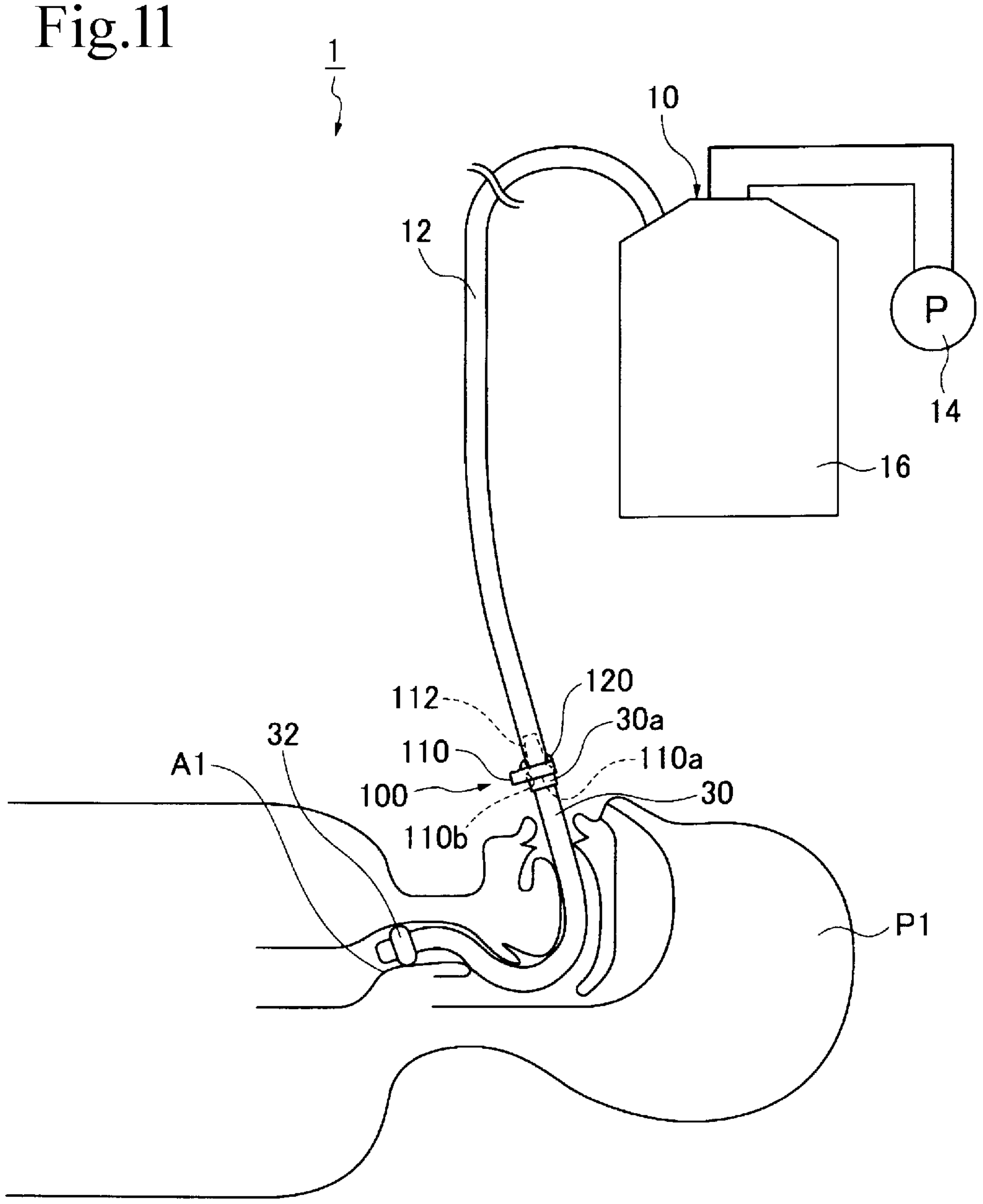
FIG. 11 is a schematic diagram illustrating a configuration of a suction-target suction system according to yet another embodiment of the present invention that uses the suction-target guide pipe according to the first embodiment of the present invention.

As an embodiment of the suction-target guide pipe 100, the suction-target suction system 1, and the suction-target guiding method using the suction-target suction system 1, the suction-target suction system 1 of the present embodiment may be configured as illustrated in FIG. 11. In other words, as illustrated in FIG. 11, the suction-target suction system 1 of the present embodiment is used when a suction target such as sputum is suctioned and removed from the patient P1 who is in an intensive care unit (ICU) or the like after surgery and under the control of a respirator with a tracheal tube 30 intubated into the trachea A1 through the mouth of the patient P1. More specifically, the tracheal tube 30 is inserted toward the trachea A1 and fixed in place at its distal end side by a cuff 32, and the suction-target guide pipe 100 is brought into close contact with a joint portion 30*a* of the tracheal tube 30 that is provided on the proximal end side of the tracheal tube 30 so as to guide the suction target such as sputum toward the upper respiratory tract side. Then, the suction target guided to the upper respiratory tract side is suctioned by a suction device such as a suction catheter, so that the suction target is removed.

Note that, in the present embodiment, the diameter of the opening 110*a* of the suction-target guide pipe 100 is slightly larger than the diameter of the joint portion 30*a* of the tracheal tube 30 so as to allow leeway. More specifically, in the case where the outer diameter of the joint portion 30*a* of the tracheal tube 30 is, for example, 15 mm, the inner diameter of the opening 110*a* of the suction-target guide pipe 100 is set to 17 mm, so that the joint portion 30*a* and the suction-target guide pipe 100 may be easily brought into close contact with each other, and the probability that the patient will have a suffocation accident as a result of an excessive operation for bringing these members into close contact with each other, that is, connection of these members, can be reduced.

Operations and effects of the suction-target guide pipe 100 and the suction-target suction system 1 according to the embodiments of the present invention will now be described.

In the suction-target guide pipe 100 of the present embodiment, the connection pipe 112 of the guide-pipe main body 110 that is connected to the end of the suction tube 12 of the suction device 10 is formed so as to have a diameter decreasing toward the distal end thereof. Accordingly, the degree of contact between the connection pipe 112 of the guide-pipe main body 110 and the end of the suction tube 12 increases, and thus, a suction pressure from the suction device 10 is reliably applied to the inside of the suction-target guide pipe 100. As a result, a suction target such as sputum that is present in the lower respiratory tract, which extends from the trachea to the terminal bronchioles, can be efficiently guided to the upper respiratory tract side so as to be easily suctioned by a suction device, such as a suction catheter, through the suction-target guide pipe 100, so that, the suction efficiency is improved.

In other words, after the suction-target guide pipe 100 of the present embodiment has been attached to the end of the suction tube 12 of the suction device 10, the suction-target guide pipe 100 is brought into contact with a human-body-wearable ventilation member, such as the tracheal tube 30, the tracheal cannula 20, or the artificial ventilation mask 50, which is attached to a patient, such that the suction-target guide pipe 100 and the human-body-wearable ventilation member communicate with each other, and this facilitates guiding of a suction target to the upper respiratory tract side, so that the suction target can be guided to the upper respiratory tract side by a simple technique. Therefore, minimally invasive suctioning of the suction target from the upper respiratory tract side (minimally invasive discharge of the suction target to the outside the body) can be easily performed.

Vacuuming using the negative pressure from the suction device 10 can also be performed by bringing the suction tube 12 into close contact with a human-body-wearable ventilation member such as the tracheal tube 30 or the tracheal cannula 20. However, when the suction tube 12 is used by being cut with scissors, the cross-sectional shape of the suction tube 12 is irregular, and also the tube diameter of the suction tube 12 varies. Consequently, it is difficult to bring the suction tube 12 into close contact with the human-body-wearable ventilation member, such as the tracheal tube 30 or the tracheal cannula 20, and the effect of vacuuming varies depending on the skill of a practitioner. Thus, in the present embodiment, the degree of contact between the suction tube 12 and a human-body-wearable ventilation member, such as the tracheal tube 30 or the tracheal cannula 20, is increased by attaching the suction-target guide pipe 100, in which the connection pipe 112 is included in the guide-pipe main body 110, to the end of the suction tube 12 so as to increase the degree of contact between the suction tube 12 and the connection pipe 112. Therefore, according to the present embodiment, even if a practitioner is not skilled, vacuuming effect equivalent to that obtained by a skilled practitioner can be obtained, and vacuuming equivalent to that performed by a skilled practitioner can be performed by anyone.

In the present embodiment, the lid 120 is openable and closable with respect to the opening 110*a* of the guide-pipe main body 110, which includes the connection pipe 112. Thus, when the lid 120 is opened with respect to the opening 110*a* of the guide-pipe main body 110, the inner peripheral surface 110*b* of the guide-pipe main body 110 may be easily brought into close contact with one of various human-body-wearable ventilation members such as the tracheal cannula 20 that is attached to the patient P1.

Thus, by increasing the airtightness between the suction-target guide pipe 100 and various human-body-wearable ventilation members such as the tracheal cannula 20, the suction pressure from the suction device 10 is easily transmitted to various human-body-wearable ventilation members through the suction-target guide pipe 100, and thus, a suction target such as sputum or a foreign matter in the periphery of the lower respiratory tract, which extends from the trachea A1 to the terminal bronchioles, can be easily moved to the upper respiratory tract side. In addition, the suction target guided to the upper respiratory tract side comes close to a suction device, such as a suction catheter, that is used when the suction target is suctioned, and thus, the suction target can be easily suctioned, so that the efficiency with which the suction target is suctioned is improved.

In addition, in the present embodiment, when the lid 120 is closed with respect to the opening 110*a* of the guide-pipe main body 110, the inner peripheral surface 110*b* of the guide-pipe main body 110 and the inner peripheral surface 120*b* of the lid 120 form a continuous curved surface, and an olive-shaped space is formed in the suction-target guide pipe 100. Thus, when a suction operation is performed by closing the lid 120 with respect to the opening 110*a* of the guide-pipe main body 110 in a state where the connection pipe 112 of the guide-pipe main body 110 of the suction-target guide pipe 100 is connected to the suction tube 12 and bringing the suction-target guide pipe 100 close to the nasal cavity of the patient P1 in a state where the end cap 130 is opened with respect to the opening 120*a* of the lid 120, a suction target such as nasal discharge can be guided to the front side of the nasal cavity through the olive-shaped space and suctioned efficiently as in the case of using a so-called olive-shaped pipe.

In addition, in the present embodiment, in the case where the outer diameter of a suction port of the tracheal cannula 20 is small, vacuuming and a suction operation are performed by closing the lid 120 with respect to the guide-pipe main body 110 and bringing the tracheal cannula 20 into close contact with the opening 120*a* of the lid 120, so that a suction target can be suctioned after being guided to the upper respiratory tract side, and thus, the suction efficiency can be improved.

As described above, in the present embodiment, by opening and closing the lid 120 of the suction-target guide pipe 100 in accordance with the types or forms of the suction tube 12 of the suction device 10 and various human-body-wearable ventilation members such as the tracheal cannula 20 and a suction catheter that are used when suctioning a suction target such as sputum from the patient P1, the contact portions of the suction-target guide pipe 100 and the various human-body-wearable ventilation members can be changed, so that the degree of contact between them can be increased. Thus, the suction-target guide pipe 100 of the present embodiment functions as a guide pipe that guides a suction target such as sputum that is present on the lower respiratory tract side to the upper respiratory tract side by being attached as an attachment that is interposed between various human-body-wearable ventilation members that are used by, for example, being inserted into or attaching to the patient P1, and the suction tube 12 of the suction device 10, and suctioning of the suction target such as sputum guided to the upper respiratory tract side can be easily performed, so that minimally invasive suctioning of a suction target such as sputum can be achieved.

In other words, in general, when a suction catheter connected to a suction tube is inserted into the respiratory tract so as to perform sputum suction, a sufficient suction effect cannot be obtained unless an end of the suction catheter reaches the sputum to be suctioned. In addition, in the case of blindly performing an operation of inserting the suction catheter, there is a concern about the risk of damaging the respiratory tract of the patient as a result of irritation of the respiratory tract due to deep insertion of the suction catheter. In contrast, mechanical insufflation-exsufflation (MI-E) can achieve minimally invasive sputum suction in a short time. However, a device that performs mechanical insufflation-exsufflation (MI-E) is configured to electromechanically control inhalation and exhalation pressures, and thus, it is expensive. In addition, since technical skills are required for a suction operation of applying positive pressure and then applying negative pressure mechanically, it is difficult to perform the suction operation without training the operation.

In contrast, by attaching the suction-target guide pipe 100 of the present embodiment to the end of the suction tube 12 and then using the suction-target guide pipe 100 as an attachment that is brought into close contact with a human-body-wearable ventilation member such as the tracheal cannula 20 or the tracheal tube 30 that is attached to the patient P1, the degree of contact between the suction-target guide pipe 100 and the suction tube 12 and the degree of contact between the suction-target guide pipe 100 and the human-body-wearable ventilation member can both be increased. Therefore, the suction force (negative pressure) of the suction device 10 does not leak from the portion in which the suction-target guide pipe 100 is in close contact with the suction tube 12 or the human-body-wearable ventilation member and is transmitted to the human-body-wearable ventilation member such as the tracheal cannula 20 or the tracheal tube 30.

In other words, after the connection pipe 112 of the suction-target guide pipe 100 has been connected to the end of the suction tube 12, by bringing the inner peripheral surface 110*b* of the guide-pipe main body 110 of the suction-target guide pipe 100, the inner peripheral surface 110*b* being on the side on which the opening 110*a* is formed, into close contact with the human-body-wearable ventilation member such as the tracheal cannula 20 or the tracheal tube 30 that is attached to the patient P1, a suction target such as sputum or a foreign matter in the periphery of the lower respiratory tract of the patient P1 is guided to the upper respiratory tract side by vacuuming through the guide-pipe main body 110. Thus, the suction target that has moved to the upper respiratory tract side can be easily suctioned and removed by using a suction device, such as a suction catheter. In particular, in the present embodiment, as described above, pressure ventilation with a positive pressure is performed by using a bag valve mask or the like before the vacuuming operation with a negative pressure and after the operation of suctioning the suction target, which has been guided to the upper respiratory tract side, so that minimally invasive suction and removal of a suction target such as sputum can be easily performed.

As described above, by attaching the suction-target guide pipe 100 of the present embodiment to the end of the suction tube 12 and using the suction-target guide pipe 100 as an attachment that is brought into close contact with a human-body-wearable ventilation member that is attached to the patient P1, a suction target can be easily guided to the upper respiratory tract side, and this makes it easier to suction the suction target guided to the upper respiratory tract side, so that the suction efficiency is improved. In particular, in the case of performing sputum suction, if a method of inducing a cough by blindly inserting a suction catheter deep into the respiratory tract of the patient P1 is employed, the patient P1 experiences pain, and in addition, there is a risk of serious complications such as a cerebrovascular accident due to elevated blood pressure and respiratory tract injury. In contrast, in the present embodiment, the risk of such pain and complications can be reduced.

In addition, in the present embodiment, since efficient sputum suction is performed without using an expensive device that performs mechanical insufflation-exsufflation (MI-E), minimally invasive suction and removal of a suction target such as sputum capable of reducing the amount of pain or the like experienced by the patient P1 and improving the quality of life (QOL) of patient P1 at a lower cost can be achieved. Furthermore, in the present embodiment, since the suction-target guide pipe 100 has a simple configuration, mass production of the suction-target guide pipe 100 can be performed at a low price, and the time and effort needed for preparation and cleaning up can be reduced compared with the case of a sputum suction method using mechanical insufflation-exsufflation (e.g., MI-E) or a device (e.g., a bronchoscope or a percussive ventilator). In the present embodiment, a suction target can be guided more reliably than in the case of using a sputum suction method such as postural drainage or squeezing (a manual breathing assist technique). In particular, in the case where a patient has been bedridden for a long time, postural drainage and squeezing have the risk of bone fracture that occurs as a result of changing the patient's posture. However, vacuuming according to the present embodiment can obtain the effect of suctioning a suction target regardless of the patient's posture, and thus, the risk of bone fractures that occurs as a result of changing the patient's posture can be reduced.

In the present embodiment, since the lid 120 is openable and closable with respect to the guide-pipe main body 110 by the hinge mechanism 118, the lid 120 can be easily opened and closed with one hand during the period when the suction-target guide pipe 100 is used in sputum suction or the like, and thus, the efficiency with which sputum suction or the like is performed is improved. In addition, after the suction-target guide pipe 100 has been used, maintenance such as cleaning can be easily performed by opening the lid 120 with respect to the guide-pipe main body 110.

Furthermore, in the present embodiment, the holder 116 that is capable of holding a tubular member such as the suction tube 12 is provided at the end of the lower-end-side outer periphery of the guide-pipe main body 110. Thus, after an operation of suctioning sputum has been completed, the suction tube 12 can be fixed in place such that an end of the suction tube 12 faces upward in order to prevent a discharged fluid remaining in the suction tube 12, which has been used, from dripping. In particular, in the present embodiment, since the holder 116 of the guide-pipe main body 110 has the inner peripheral surface **116*b* whose diameter increases from the proximal end side to the distal end side, the suction tube 12 made of a resin having flexibility can be easily fit into the holder 116 from the proximal end side to the distal end side of the holder 116** so as to be fixed in place.

In the present embodiment, the guide-pipe main body 110, the lid 120, the hinge mechanism 118, the end cap 130, and the connection cord 114 that are included in the suction-target guide pipe 100 are integrally formed into one member made of a resin. Thus, the suction-target guide pipe 100 including these components can be easily manufactured in an unfolded state by performing injection molding using a thermoplastic resin. In this case, by forming the suction-target guide pipe 100 in the unfolded state as an integrally molded body while paying attention to the arrangements of the hinge mechanism 118 connecting the guide-pipe main body 110 and the lid 120 to each other and the connection cord 114 connecting the lid 120 and the end cap 130 to each other, the suction-target guide pipe 100 becomes easy to handle, and its usability when a medical worker or the like uses the suction-target guide pipe 100 is improved. In particular, in the case where the suction-target guide pipe 100 is formed of a plurality of separable components, there is a possibility that the components will be lost. However, since the suction-target guide pipe 100 of the present embodiment is formed of a single resin molded member, it is unlikely that the components will be lost.

Note that, although the embodiments of the present invention have been described above, those skilled in the art will be able to understand that many modifications may be made without substantially departing from the new matters and effects of the present invention. Therefore, all such modifications are included in the scope of the present invention.

For example, a term that is mentioned with a different term having a broader meaning or the same meaning at least once in the specification or the drawings can be replaced with the different term at any position in the specification or the drawings. In addition, the configuration and operation of the suction-target guide pipe and the configuration and operation of the suction-target suction system are not limited to the above-described embodiments of the present invention, and various modifications can be made.

What is claimed is:

1. A suction-target guide pipe comprising:

a guide-pipe main body that includes a connecting portion to be connected to a suction tube of a suction device, and a first opening provided to a portion opposite to the connecting portion of the guide-pipe main body, wherein the suction device is configured to guide a suction target in a patient's trachea to an upper respiratory tract side, or to guide nasal discharge in the patient's nasal cavity to a front side of the nasal cavity, and a lid that is configured to open and close with respect to the first opening and that has an outer peripheral surface and a second opening on a distal end, the outer peripheral surface being formed of a tapered surface whose diameter increases from the distal end to a proximal end thereof, wherein the tapered surface is formed at an outer edge of the second opening, the tapered surface being configured to be brought into close contact with the patient's nasal cavity, thereby enabling suction of the nasal discharge in the patient's nasal cavity through the second opening, wherein an inner peripheral surface of the guide-pipe main body is a continuously curved surface extending over its entire circumference, whose diameter decreases from the first opening of the guide-pipe main body toward a proximal end of the connecting portion, and the inner peripheral surface has a contact portion configured to be brought into contact with an end of a human-body-wearable ventilation member configured to be attached to the patient, and wherein a diameter of the first opening is larger than a diameter of the end of the human-body-wearable ventilation member to allow leeway therebetween, and the first opening and the end of the human-body-wearable ventilation member are configured to be brought into close contact without being connected with friction.

2. The suction-target guide pipe according to claim 1, wherein the lid is openable and closable with respect to a portion that faces the connecting portion of the guide-pipe main body.

3. The suction-target guide pipe according to claim 1, wherein an inner peripheral surface of the lid is formed of a curved surface whose diameter decreases from the proximal end to the distal end and is a curved surface that is contiguous to the inner peripheral surface of the guide-pipe main body.

4. The suction-target guide pipe according to claim 1, wherein the connecting portion of the guide-pipe main body is a connection pipe whose diameter decreases toward a distal end of the connection pipe.

5. The suction-target guide pipe according to claim 1, wherein a holder that is capable of holding a tubular member is provided at an end of an outer periphery of the guide-pipe main body on a lower end side of the guide-pipe main body.

6. The suction-target guide pipe according to claim 5, wherein the holder is formed in such a manner as to have an inner peripheral surface whose diameter increases from its proximal end to its distal end.

7. The suction-target guide pipe according to claim 1, wherein the lid is a hinge cap that is openable and closable with respect to the guide-pipe main body by a hinge mechanism.

8. The suction-target guide pipe according to claim 1, further comprising:

an end cap that is movable so as to open and close the second opening of the lid via a connection cord that is connected to an end of the lid.

9. The suction-target guide pipe according to claim 7, further comprising:

an end cap that is movable so as to open and close the second opening of the lid via a connection cord that is connected to an end of the lid.

10. The suction-target guide pipe according to claim 9, wherein the guide-pipe main body, the lid, the hinge mechanism, the end cap, and the connection cord are formed of an integrally molded body.

11. The suction-target guide pipe according to claim 9, wherein the hinge mechanism is provided so as to be capable of performing opening and closing operations in directions that are perpendicular to a direction in which a holder of the guide-pipe main body is oriented, and wherein the connection cord is provided so as to be located at a position facing the holder and so as to extend in a direction perpendicular to a direction in which the hinge mechanism of the lid is oriented when viewed in plan view from the connecting portion in a state where the lid is closed with respect to the guide-pipe main body.

12. A suction-target suction system that sucks in a suction target in a living body, the suction-target suction system including:

a suction device that includes a suction tube; and a suction-target guide pipe according to claim 1 that is connected to an end of the suction tube.

13. The suction-target guide pipe according to claim 1, wherein the guide-pipe main body has an engagement recess formed on a proximal end, and an engagement projection of the lid that is formed on the proximal end of the lid is configured to be fitted into the engagement recess.

14. The suction-target guide pipe according to claim 13, wherein the inner peripheral surface of the guide-pipe main body is a curved surface whose diameter decreases from an upper end of the engagement recess to the proximal end of the connecting portion.

15. The suction-target guide pipe according to claim 1, wherein the lid has an inner peripheral surface that is formed of a curved surface whose diameter decreases from the proximal end to the distal end.

16. The suction-target guide pipe according to claim 15, wherein the curved surface of the inner peripheral surface of the lid is contiguous to the inner peripheral surface of the guide-pipe main body when the lid is closed with respect to the guide-pipe main body.

17. The suction-target guide pipe according to claim 1, wherein the lid has a long cap shape, comprising an elongated hollow pipe portion extending between the distal end and the proximal end, the distal end being configured to reach an oral cavity of the patient's upper respiratory tract and having a length sufficient to suction the suction target through the second opening.

* * * * *